US009656967B2

(12) United States Patent
Fujiwara et al.

(10) Patent No.: US 9,656,967 B2
(45) Date of Patent: May 23, 2017

(54) METHOD FOR PRODUCING HALOHYDANTOIN COMPOUND

(71) Applicant: NIPPOH CHEMICALS CO., LTD., Tokyo (JP)

(72) Inventors: Naoki Fujiwara, Isumi (JP); Keisuke Takahashi, Tokyo (JP)

(73) Assignee: NIPPOH CHEMICALS CO., LTD., Tokyo (JP)

( * ) Notice: Subject to any disclaimer, the term of this patent is extended or adjusted under 35 U.S.C. 154(b) by 0 days.

(21) Appl. No.: 14/350,096

(22) PCT Filed: Nov. 15, 2013

(86) PCT No.: PCT/JP2013/080919
§ 371 (c)(1),
(2) Date: May 29, 2015

(87) PCT Pub. No.: WO2014/147889
PCT Pub. Date: Sep. 25, 2014

(65) Prior Publication Data
US 2015/0376137 A1 Dec. 31, 2015

(30) Foreign Application Priority Data
Mar. 19, 2013 (JP) ................. 2013-056989

(51) Int. Cl.
*C07D 233/82* (2006.01)
*C07D 233/72* (2006.01)

(52) U.S. Cl.
CPC ......... *C07D 233/82* (2013.01); *C07D 233/72* (2013.01)

(58) Field of Classification Search
CPC ..................... C07D 233/72; C07D 233/82
See application file for complete search history.

(56) References Cited

U.S. PATENT DOCUMENTS

| 4,621,096 A | 11/1986 | Cole |
| 5,780,641 A | 7/1998 | Yerushalmi et al. |
| 2001/0010165 A1 | 8/2001 | Kubota et al. |
| 2009/0259050 A1 | 10/2009 | Inoue et al. |
| 2010/0137349 A1* | 6/2010 | Jain ................. A01N 43/76 514/278 |
| 2011/0087031 A1 | 4/2011 | Inoue et al. |
| 2011/0092714 A1 | 4/2011 | Inoue et al. |
| 2011/0144350 A1 | 6/2011 | Inoue et al. |

FOREIGN PATENT DOCUMENTS

| JP | 34-10025 | 11/1959 |
| JP | 9-316057 | 12/1997 |
| JP | 2001-334098 | 12/2001 |
| JP | 2002-30072 | 1/2002 |
| JP | 2013-23475 | 2/2013 |
| WO | 97/43264 | 11/1997 |
| WO | 01/52656 | 7/2001 |
| WO | 01/53270 | 7/2001 |
| WO | 2007/026766 | 3/2007 |

OTHER PUBLICATIONS

Salellas, J. F. "Nuclear halogenation with 1,3-dibromo-5,5-dimethylhydantoin." An. Asoc. Quim. Argent. 19541, 39, 175-183.*
Harrison, E. I. "Environmental Assesment for Dimethylhydantoin (DMH) Food-Contact Notification (FCN)" May 12, 2010 [online]: Federal Drug Administration [retrieved on Oct. 17, 2016]. Retrieved from <http://www.fda.gov/downloads/Food/FoodIngredientsPackaging/EnvironmentalDecisions/UCM207366.pdf>.*
Whitehead et al. "A simple and expedient method for the preparation of N-chlorohydantoins" Tetrahedron Lett. 2009, 50, 656-658.*
International Preliminary Report on Patentability, International Patent Application No. PCT/JP2013/080919, mailed Oct. 1, 2015, seven pages.
International Search Report, International Patent Application No. PCT/JP2013/080919, mailed Dec. 17, 2013.
Orazi O., et al., "N-Idohydantoins. II. Iodinations with 1,3-Diiodo-5,5-dimethylhydantoin", J. Org. Chem. 1965, vol. 30, p. 1101-1104.
Yoshimura, J. Kagaku Jiten, (Second Edition) [compact edition], Morikita Shuppan Co., Ltd., Nov. 15, 2012, p. 1469-1470, column of "iodine", (Full English translation included).
Raab, Conrad E. et al. "Carbon-14 labeling of a trifluoronmethoxy group: synthesis of a substance P antagonist", Journal of Labelled Compounds and Radiopharmaceuticals, vol. 44, No. 12, Oct. 30, 2001, pp. 815-829.
European Search Report, EP Patent Application No. 13878784.1, mailed Jul. 28, 2016, 9 pages.
Office Action, Chinese Patent Application No. 201380069768.8, mailed Mar. 2, 2016, English translation included.

* cited by examiner

*Primary Examiner* — Michael Barker
*Assistant Examiner* — Amanda L Aguirre
(74) *Attorney, Agent, or Firm* — Casimir Jones, SC

(57) ABSTRACT

A production method of the present invention is a method for producing a halohydantoin compound in which method a composition including a halohydantoin compound and an impurity is treated, the method including the step of adding the composition to a mixed solvent of water and an organic solvent and washing the composition.

7 Claims, No Drawings

METHOD FOR PRODUCING HALOHYDANTOIN COMPOUND

TECHNICAL FIELD

The present invention relates to a method for producing a halohydantoin compound.

BACKGROUND ART

A halohydantoin compound has been widely used as a sensitizer for a photograph or the like or as a halogenating agent or an oxidizing agent for use in a process of producing a medicinal product, an agricultural chemical, a compound, or the like. In particular, 1,3-diiodo-5,5-dimethylhydantoin, which is a halohydantoin compound, is considered as a promising compound, as 1,3-diiodo-5,5-dimethylhydantoin is high in iodine content and a more economical method for producing 1,3-diiodo-5,5-dimethylhydantoin has been disclosed. As a method for producing 1,3-diiodo-5,5-dimethylhydantoin, for example, a method including the step of causing 5,5-dimethylhydantoin and iodine monochloride to react with each other in the presence of a base in a mixed solvent of an aqueous solution and an organic solvent and a refining method have been disclosed (see, for example, Patent Literature 1 and Non Patent Literature 1).

Non Patent Literature 1 describes the following method: 5,5-dimethylhydantoin and iodine monochloride are reacted with each other with use of a sodium hydroxide aqueous solution and carbon tetrachloride. The resulting crystals are washed with water, and are further washed with anhydrous ethyl acetate. After that, the crystals are dried at 60° C. under reduced pressure. Thereby, 1,3-diiodo-5,5-dimethylhydantoin is refined. Non Patent Literature 1 further states that the resulting 1,3-diiodo-5,5-dimethylhydantoin is a reagent so stable that it can be preserved in a desiccator in a dark place without recrystallizing.

Further, Patent Literature 1 gives the following description: First, 5,5-dimethylhydantoin and iodine monochloride are reacted with each other in a sodium hydroxide aqueous solution with use of N,N-dimethylformamide or an n-butyl acetate solvent. Next, the precipitated crystals as a result of the reaction are collected by filtration, and then, dried under reduced pressure, thereby being refined.

CITATION LIST

Patent Literature 1

Japanese Patent Application Publication, Tokukai, No. 2002-30072 A (Publication Date: Jan. 29, 2002)

Non Patent Literature 1

ORFEO O. ORAZI., et al., N-Iodohydantoins. II. Iodinations with 1,3-Diiodo-5,5-dimethylhydantoin, *J. Org. Chem.*, 1965, Vol. 30, p. 1101-1104

SUMMARY OF INVENTION

Technical Problem

With the refining method described in Non Patent Literature 1, 1,3-diiodo-5,5-dimethylhydantoin contains 65% of effective iodine, and the yield of 1,3-diiodo-5,5-dimethylhydantoin is as low as 75%. Non Patent Literature 1 makes no mention of the purity of 1,3-diiodo-5,5-dimethylhydantoin.

Further, Patent Literature 1 makes no mention of the purity of 1,3-diiodo-5,5-dimethylhydantoin that is obtained by the refining method described therein.

The inventors of the present invention diligently studied the methods for refining a halohydantoin compound described in these literatures. As a result, the present inventors finally found the following problems:

A halohydantoin compound is so unstable at normal temperature that the halohydantoin compound needs to be refrigerated for preservation. Further, when suspended in water, a halohydantoin compound gradually decomposes to liberate elemental halogen. Furthermore, when heated in the state of being a wet material containing a certain or lager amount of a mixed liquid component such as a mixture of water and an organic solvent, a halohydantoin compound is problematically more unstable. In addition, when a halohydantoin compound is dried under reduced pressure, elemental halogen caused by pyrolysis is sublimated, so that the sublimated elemental halogen is solidified in a reduced pressure line and that the solidified elemental halogen blocks the reduced pressure line. As a result, the pressure is not reduced, the pressure inside the dryer was raised, and the temperature inside the dryer was raised. The halohydantoin compound in turn becomes even more unstable. The halohydantoin compound consequently decomposes to liberate a hydantoin compound and elemental halogen. This causes a decrease in purity of the halohydantoin compound. Further, the elemental halogen thus liberated undesirably causes coloring of the halohydantoin compound and corrosion of refining equipment.

The present invention has been made in view of the foregoing problems, and it is an object of the present invention to provide a method for producing a halohydantoin compound by removing an impurity from a composition containing the halohydantoin compound while inhibiting the halohydantoin compound from decomposing to invite coloring of the halohydantoin compound and corrosion of the equipment.

Solution to Problem

In order to solve the above problem, a production method of the present invention is a method for producing a halohydantoin compound in which method a composition including a halohydantoin compound and an impurity is treated, the method comprising the step of: washing the composition by adding the composition to a mixed solvent of water and an organic solvent and washing the composition with the mixed solvent.

Advantageous Effects of Invention

The present invention makes it possible to advantageously produce a halohydantoin compound by removing an impurity from a composition containing the halohydantoin compound while inhibiting the halohydantoin compound from decomposing to invite coloring of the halohydantoin compound and corrosion of the equipment.

DESCRIPTION OF EMBODIMENTS

A production method according to the present invention is a method for producing a halohydantoin compound in which method a composition including a halohydantoin compound and an impurity is treated. The method includes a washing step of adding the composition to a mixed solvent of water and an organic solvent and washing the composition with the mixed solvent.

As described above, a halohydantoin compound is unstable in a state where it is a wet material containing a liquid component to some extent. There is a known method for drying such a wet material. However, in a case where the wet material is heated and dried under reduced pressure so as to be refined, the halohydantoin compound becomes more unstable in state. The halohydantoin compound is consequently decomposed so that a hydantoin compound and elemental halogen are liberated from each other. As a result, the halohydantoin compound has decreased purity and is colored by the elemental halogen liberated.

The inventors of the present invention have diligently examined the above problem to find a solution thereto, and have consequently found that by washing, with a mixed solvent of water and an organic solvent, a halohydantoin compound having decreased purity and significant coloring, it is possible to increase purity of the halohydantoin compound and reduce coloring thereof. In other words, the present invention can provide a method for producing a halohydantoin compound having high purity and less coloring.

(Composition)

The production method of the present invention treats a composition including a halohydantoin compound and an impurity. The composition contains the impurity in an amount that has a lower limit value of preferably 4 weight %, more preferably 5 weight %, or even more preferably 6 weight % impurity in an amount that has an upper limit value of preferably 30 weight %, more preferably 25 weight %, or even more preferably 20 weight % relative to the entire composition. In a case where a composition including an impurity in an amount within the above range is treated by the production method of the present invention, it is possible to produce a halohydantoin compound having reduced impurity content and high purity.

The composition preferably has a color tone having an L* value of not greater than 70, an a* value of not less than 5, and a b* value of not greater than 14 in the L*a*b* color system (CIE 1976 L*a*b* color space). In a case where a composition having significant coloring is treated by the production method of the present invention, it is possible to produce a halohydantoin compound having less coloring.

Note that the present specification uses the term "composition" to refer to a composition including an impurity in an amount within the above range, and may simply use the term "halohydantoin compound" to refer to a composition including an impurity in an amount of less than 4 weight % as a result of treatment by the production method of present invention.

The method of the present invention for producing a halohydantoin compound is intended to produce, for example, a halohydantoin compound represented by a chemical formula I below. The chemical formula I below may have any combination of $R_1$, $R_2$, $X_1$, and $X_2$ within the above range.

Chem. 1

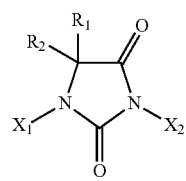

(I)

where $R_1$ and $R_2$ are either identical to or different from each other, and are (i) each independently H, a substituted or unsubstituted C1 to C10 aliphatic hydrocarbon group, a substituted or unsubstituted C3 to C10 alicyclic hydrocarbon group, or a substituted or unsubstituted C6 to C10 allyl group or aralkyl group, more preferably H or a C1 to C8 aliphatic hydrocarbon group, or even more preferably H or a methyl group, or (ii) most preferably both methyl groups; and $X_1$ and $X_2$ are either identical to or different from each other, and are (i) each independently H or a halogen atom, more preferably H, Br, or I, or even more preferably H or I, or (ii) most preferably both I, excluding a halohydantoin compound wherein $X_1$ and $X_2$ are both H.

Specific examples of the halohydantoin compound encompass 1-bromohydantoin, 1-iodohydantoin, 3-bromohydantoin, 3-iodohydantoin, 1,3-dibromohydantoin, 1,3-diiodo hydantoin, 1-bromo-5-methylhydantoin, 1-iodo-5-methylhydantoin, 3-bromo-5-methylhydantoin, 3-iodo-5-methylhydantoin, 1,3-dibromo-5-methylhydantoin, 1,3-diiodo-5-methylhydantoin, 1-bromo-5,5-dimethylhydantoin, 1-iodo-5,5-dimethylhydantoin, 3-bromo-5,5-dimethylhydantoin, 3-iodo-5,5-dimethylhydantoin, 1,3-dibromo-5,5-dimethylhydantoin, and 1,3-diiodo-5,5-dimethylhydantoin.

A method for preparing the halohydantoin compound is not particularly limited to any specific one. The halohydantoin compound may be synthesized by a conventionally publicly known method. The description below deals with an example method for synthesizing the halohydantoin compound.

First, a hydantoin compound and a halogen compound such as iodine monochloride are reacted with each other in an aqueous solution in the presence of a base. As a result, a wet material including a halohydantoin compound is obtained. Since a halohydantoin compound in this state is unstable, the wet material is then heated to be dried so that a liquid component is removed. A method for heating the wet material to dry it may be a drying method that is industrially generally used. An example method is a method for heating the wet material to dry it under reduced pressure with use of a conical vacuum dryer. A halohydantoin compound synthesized as such may contain an impurity in a large amount, and may be significantly colored. The present invention is intended to treat such a halohydantoin compound or composition.

The impurity may be, for example, at least one of elemental halogen, a hydantoin compound, and an inorganic salt. Elemental halogen and a hydantoin compound may be produced in a case where they were unreacted by the above synthesis method or liberated as a result of decomposition during the heating of the wet material for drying it. The elemental halogen is, for example, iodine, bromine, or chlorine. The hydantoin compound is, for example, hydantoin, 1-methylhydantoin, 5-methylhydantoin, or 5,5-dimethylhydantoin. An inorganic salt is produced as a by-product of the base and halogen compound for use in synthesis of the halohydantoin compound. The inorganic salt is, for example, lithium chloride, sodium chloride, potassium chloride, or magnesium chloride.

Note that the production method of the present invention is intended to treat not only a composition produced as a result of heating the wet material to dry it by the synthesis method, but also, for example, a composition in the state of a wet material produced through a synthesis reaction.

The composition may further contain a component other than the impurity. Examples of such a component encompass components such as water and an organic solvent. The production method of the present invention is also intended to treat such a composition.

(Washing Step)

The washing step is a step of adding the above composition to a mixed solvent of water and an organic solvent and washing the composition with the mixed solvent. As described above, the present invention washes the composition with use of a mixed solvent prepared in advance by mixing water and an organic solvent with each other. In other words, the present invention neither uses water alone or an organic solvent alone, nor uses water and an organic solvent separately. Since the present invention washes a composition with use of a mixed solvent, the present invention can not only improve purity but also produce a halohydantoin compound having less coloring. Stated differently, the production method of the present invention is a method for regenerating a halohydantoin compound that does not meet a product standard.

A method for the washing is not particularly limited to any specific one. The composition may simply be washed by a conventionally publicly known method. For example, it is possible to wash the composition by (i) putting, in a reaction container equipped with a stirrer, water and an organic solvent so as to prepare a mixed solvent, (ii) putting a composition in the reaction container, and (iii) stirring the mixture. However, the washing method is not limited to such a method, and may alternatively be a method of, for example, first putting a composition in a Nutsche or a centrifuge and washing the composition with use of a mixed solvent passing therethrough.

During the washing step, the mixed solvent has a temperature having (i) a lower limit value of preferably −10° C., more preferably −5° C., or even more preferably 0° C. and having (ii) an upper limit value of preferably 50° C., more preferably 40° C., or even more preferably 30° C. In a case where the mixed solvent has a temperature of not less than −10° C., it is advantageously possible to produce high washing effect, increase purity, and reduce coloring. In a case where the mixed solvent has a temperature of not greater than 50° C., it is advantageously possible to prevent decomposition of the halohydantoin compound. By washing a composition within such a low temperature range, it is possible to suppress decomposition of the halohydantoin compound contained in the composition and thus to produce a halohydantoin compound having high purity.

The washing step is carried out during a time period having (i) a lower limit of preferably 1 minute, more preferably 10 minutes, or even more preferably 20 minutes and having (ii) an upper limit of preferably 24 hours, more preferably 12 hours, or even more preferably 6 hours. By treating the composition within such a time period, it is possible to increase purity and reduce coloring, and further to prevent decomposition of the halohydantoin compound.

The mixed solvent contains the organic solvent in a content having (i) a lower limit value of preferably 10 weight %, more preferably 12 weight %, or even more preferably 15 weight % relative to the entire mixed solvent and having (ii) an upper limit value of preferably 90 weight %, more preferably 85 weight %, or even more preferably 80 weight % relative to the entire mixed solvent. By treating the composition with use of a mixed solvent including the organic solvent within the above range, it is possible to increase purity and reduce coloring, prevent decomposition of the halohydantoin compound, increase the yield of the halohydantoin compound, and further to give a high filterability to the composition thus treated. The organic solvent is, for example, suitably at least one of an ester solvent, an alcohol solvent, an aromatic solvent, an ether solvent, and a chlorine solvent, each having a boiling point of not less than 30° C. and not greater than 200° C.

Examples of the ester solvent encompass methyl acetate, ethyl acetate, propyl acetate, isopropyl acetate, butyl acetate, isobutyl acetate, sec-butyl acetate, tert-butyl acetate, pentyl acetate, hexyl acetate, methyl propionate, ethyl propionate, propyl propionate, butyl propionate, methyl butyrate, ethyl butyrate, propyl butyrate, and butyl butyrate.

Examples of the alcohol solvent encompass methanol, ethanol, propanol, isopropanol, butanol, isobutanol, sec-butanol, and tert-butanol.

Examples of the aromatic solvent encompass benzene, toluene, ethylbenzene, propyl benzene, cumene, butylbenzene, isobutyl benzene, sec-butyl benzene, tert-butyl benzene, o-xylene, m-xylene, p-xylene, mesitylene, 1,2,3-trimethylbenzene, 1,2,4-trimethylbenzene, o-cymene, m-cymene, and p-cymene.

Examples of the ether solvent encompass diethyl ether, dipropyl ether, isopropyl ether, methyl-tert-butyl ether, methyl cyclopentyl ether, dibutyl ether, anisole, ethyl phenyl ether, tetrahydrofuran, tetrahydropyran, and 1,4-dioxane.

Examples of the chlorine solvent encompass chloropropane, chlorobutane, chloropentane, chlorohexane, chloroheptane, chlorooctane, dichloromethane, 1,2-dichloroethane, 1,2-dichloropropane, 1,3-dichloropropane, 2,2-dichloropropane, 1,2-dichlorobutane, 1,3-dichlorobutane, 1,4-dichlorobutane, chloroform, 1,1,1-trichloroethane, 1,1,2-trichloroethane, 1,1,1,2-tetrachloroethane, 1,1,2,2-tetrachloroethane, 1,2,3-trichloropropane, and carbon tetrachloride.

Example methods for preparing the mixed solvent encompass (i) a method of mixing water and an organic solvent with each other in advance so as to prepare a mixed solvent and feeding the mixed solvent in a reaction container for washing the composition and (ii) a method of putting water and an organic solvent separately in the reaction container so as to prepare a mixed solvent.

The production method of the present invention makes it possible to produce, from a composition having a high impurity content and a poor color tone, a halohydantoin compound that has an impurity content of less than 4 weight % and that has an L* value of greater than 70, an a* value of less than 5, and a b* value of greater than 14. The halohydantoin compound thus produced contains elemental halogen, a hydantoin compound, and an inorganic salt each in a content of not greater than 1 weight %. With the production method of the present invention, it is possible to produce a halohydantoin compound having high purity and less coloring.

The description below deals in greater detail with the embodiment of the present invention on the basis of Examples below. Needless to say, the present invention is not limited to the Examples below, and may take various embodiments in terms of details. Further, the present invention is not limited to the description of the embodiment above, but may be altered in various ways by a skilled person within the scope of the claims. Any embodiment based on a proper combination of technical means disclosed is also encompassed in the technical scope of the present invention.

As described above, the production method of the present invention may preferably be arranged such that the step of washing washes the composition including the impurity in an amount within a range of not less than 4 weight % and not greater than 30 weight %.

The production method of the present invention may suitably be arranged such that the impurity is at least one of elemental halogen, a hydantoin compound, and an inorganic salt.

The production method of the present invention may preferably be arranged such that the step of washing washes the composition having an L* value of not greater than 70, an a* value of not less than 5, and a b* value of not greater than 14 in the L*a*b* color system (CIE 1976 L*a*b* color space) established by the Commission Internationale de l'Eclairage.

The production method of the present invention may suitably be arranged such that the organic solvent is at least one of an ester solvent, an alcohol solvent, an aromatic solvent, an ether solvent, and a chlorine solvent, each having a boiling point of not less than 30° C. and not greater than 200° C.

The production method of the present invention may preferably be arranged such that during the step of washing, the mixed solvent has a temperature of not less than −10° C. and not greater than 50° C.

The production method of the present invention may preferably be arranged such that the halohydantoin compound is represented by the above chemical formula I.

EXAMPLES

Respective contents of 1,3-diiodo-5,5-dimethylhydantoin, monoiodo-5,5-dimethylhydantoin, and 5,5-dimethylhydantoin were determined on the basis of an integral ratio of NMR. Elemental iodine was extracted from a sample with use of chloroform, and an amount of elemental iodine was determined by silver nitrate titration. A color tone was measured with use of spectrocolorimeter SE6000 (available from Nippon Denshoku Industries Co., Ltd.).

Production Example 1

Synthesis of 1,3-diiodo-5,5-dimethylhydantoin

First, a composition including 1,3-diiodo-5,5-dimethylhydantoin (halohydantoin compound) was produced through a procedure below.

Ion-exchange water (74.4 kg) and 12 weight % of NaOH aqueous solution (17.36 kg, 52 mol) were fed into a 200-L glass lining reaction pot, and then 5,5-dimethylhydantoin (6.7 kg, 52 mol) as a hydantoin compound was fed into the reaction pot. After that, the inside of the reaction pot was cooled to 5° C. While a temperature of a content of the reaction pot was maintained at 0 to 5° C., a butyl acetate solution (19.1 kg, 50.7 mol) of 43 weight % of iodine monochloride was dropped into the reaction pot over a duration of 60 minutes. Next, while the temperature was still maintained, a butyl acetate solution (19.1 kg, 50.7 mol) of iodine monochloride and 12 weight % of NaOH aqueous solution (17.4 kg, 52 mol) were dropped alternately. After the drop ended, a resulting product was aged at 5° C. for 30 minutes. After the aging, a reaction product was filtered with use of a centrifugal filter and watered with water. As a result, 17.6 kg of a wet material of 1,3-diiodo-5,5-dimethylhydantoin was obtained. The wet material obtained was analyzed and found to contain 1,3-diiodo-5,5-dimethylhydantoin in a content of 88.7 weight %. A portion of the wet material was dried with use of an evaporator under reduced pressure (at 4 kPa and 80° C. for 30 minutes). As a result, a product of drying 1,3-diiodo-5,5-dimethylhydantoin was obtained. The product of drying contained 1,3-diiodo-5,5-dimethylhydantoin in a content of 98.0 weight %. The product of drying had a color tone having an L* value of 88.33, an a* value of 1.70, and a b* value of 16.59.

Next, 17.5 kg of the wet material obtained was fed into a conical dryer having an internal capacity of 200 L. The conical dryer was rotated, and reduction of pressure was started. Further, a heat medium having a temperature controlled at 60 to 64° C. was passed through a jacket of the conical dryer and dried for 3.5 hours. After the drying ended, inside of the dryer was cooled to 30° C., and the reduced pressure was returned to an ordinary pressure with use of nitrogen. A product of drying 1,3-diiodo-5,5-dimethylhydantoin was obtained from the dryer. The product of drying was brown, and had a color tone having an L* value of 42.78, an a* value of 6.00, and a b* value of 5.39. The dried product contained 1,3-diiodo-5,5-dimethylhydantoin in a content of 83.8 weight %. A reason that the product of drying was colored was investigated. The investigation found that elemental iodine generated by pyrolysis of 1,3-diiodo-5,5-dimethylhydantoin was sublimated so that the sublimated elemental iodine was solidified in a reduced pressure line and that the solidified elemental iodine blocked the reduced pressure line. As a result, it was failed to reduce the pressure, thereby allowing the pressure inside the dryer to rise, and the temperature inside the dryer to rise. This rise in temperature inside the dryer caused pyrolysis of 1,3-diiodo-5,5-dimethylhydantoin and thus caused 5,5-dimethylhydantoin and elemental iodine to be liberated from each other.

Production Example 2

A wet material of 1,3-diiodo-5,5-dimethylhydantoin was obtained by a method similar to the method of Production Example 1. A portion of the wet material was sampled, and was dried with use of an evaporator under reduced pressure (at 4 kPa and 80° C. for 30 minutes). As a result, a dried product was obtained. The dried product contained 1,3-diiodo-5,5-dimethylhydantoin in a content of 96.4 weight %, was pale yellow in appearance, and had a color tone having an L* value of 88.80, an a* value of 1.54, and a b* value of 16.01.

Next, 30 g of the dried product obtained was put into a 100-ml transparent colorimetric bottle made of glass. The colorimetric bottle was then hermetically seal, and was stored for 14 days in a room having a temperature controlled at 25° C. The product stored contained 1,3-diiodo-5,5-dimethylhydantoin in a content of 94.2 weight %, had an overall appearance that was red, and had a color tone having an L* value of 65.44, an a* value of 6.69, and a b* value of 13.02. It was confirmed that particles of elemental iodine were present in the product stored.

Example 1

Example 1 produced a halohydantoin compound by treating, with a mixed solvent of an organic solvent and water, the dried product obtained in Production Example 1 above and including a halohydantoin compound.

First, air inside a reaction container equipped with a stirrer, a thermometer, a dropping funnel, and a solid input inlet and having a capacity of 300 ml was purged sufficiently with nitrogen. Next, ion-exchange water (167.2 g) was put into the reaction container through the dropping funnel, and then butyl acetate (32.8 g) was put into the reaction container through the dropping funnel so that the ion-exchange water and the butyl acetate were fed into the reaction container as a mixed solvent. The inside of the reaction container was then cooled to 4° C. After that, 30.0 g of the dried product (including 1,3-diiodo-5,5-dimethylhydantoin in a content of 83.8 weight %) that was obtained by the method of Production Example 1 above and that was brown (with a color tone having an L* value of 42.78, an a* value of 6.00, and a b* value of 5.39) was put into the reaction container. While a temperature of the inside of the reaction container was maintained at 0 to 5° C., a content of the reaction container was stirred for 30 minutes. The content of the reaction container at this stage had a pH of 2.3.

The content of the reaction container was supplied under reduced pressure over a duration of 10 seconds onto a Nutsche that included a suction bottle and a qualitative filter paper (No. 2, available from ADVANTEC) attached to the suction bottle and that had an inner diameter of 55 mm. Then, suction was continued for 5 minutes. The sucked product showed good filterability. Crystal on the filter paper was washed with water (30 g), and then the suction was continued for 20 minutes. Next, the reduced pressure was returned to an ordinary pressure, and 30.0 g of a wet material on the filter paper was taken out. The wet material thus obtained was dried with use of an evaporator under reduced pressure (at 4 kPa and 80° C. for 30 minutes). As a result, 22.8 g of a regenerated product was obtained. The regenerated product obtained was pale yellow, and had a color tone having an $L^*$ value of 86.26, an $a^*$ value of 0.44, and a $b^*$ value of 19.53. The regenerated product contained 1,3-diiodo-5,5-dimethylhydantoin in a content of 98.0 weight %, and the yield was 88.9%. No 5,5-dimethylhydantoin or elemental iodine was found in the regenerated product.

Example 2

Example 2 obtained 22.0 g of a regenerated product by a method identical to the method of Example 1 except that 27.2 g of ion-exchange water and 142.8 g of butyl acetate were fed into the reaction container as a mixed solvent. A regenerated product thus obtained was pale yellow, and had a color tone having an $L^*$ value of 86.46, an $a^*$ value of 1.19, and a $b^*$ value of 16.50. The regenerated product contained 1,3-diiodo-5,5-dimethylhydantoin in a content of 98.0 weight %, and the yield was 85.8%. No 5,5-dimethylhydantoin or elemental iodine was found in the regenerated product.

Example 3

In Example 3, a reaction container was similar to that fed to the reaction container used in Example 1. Air inside of the reaction container was purged sufficiently with nitrogen. Ion-exchange water (153.0 g) was fed into the reaction container through a dropping funnel, and then methanol (17.0 g) was fed into the reaction container through the dropping funnel. The inside of the reaction container was cooled to 2° C. After that, 30 g of a dried product (containing 1,3-diiodo-5,5-dimethylhydantoin in a content of 91.0 weight %) thus obtained by a method identical to the method of Production Example 1 and that was brown (with a color tone having an $L^*$ value of 55.14, an $a^*$ value of 5.47, and a $b^*$ value of 8.73) was put into the reaction container. While a temperature of the inside of the reaction container was maintained at 1 to 2° C., a content of the reaction container was stirred for 45 minutes. The content of the reaction container at this stage had a pH of 2.3. The content of the reaction container was supplied under reduced pressure over a duration of 10 seconds onto a Nutsche that included a suction bottle and a qualitative filter paper (No. 2, available from ADVANTEC) attached to the suction bottle and that had an inner diameter of 55 mm. Then, suction was continued for 5 minutes. The sucked product showed good filterability. Crystal on the filter paper was washed with 30 g of water, and then the suction was continued for 45 minutes. Next, the reduced pressure was returned to an ordinary pressure, and 27.5 g of a wet material on the filter paper was taken out. The wet material thus obtained was dried with use of an evaporator under reduced pressure (at 4 kPa and 80° C. for 30 minutes). As a result, 24.6 g of a regenerated product was obtained. The regenerated product obtained was pale yellow, and had a color tone having an $L^*$ value of 86.75, an $a^*$ value of 1.36, and a $b^*$ value of 15.82. The regenerated product contained 1,3-diiodo-5,5-dimethylhydantoin in a content of 98.4 weight %, and the yield was 88.6%. No 5,5-dimethylhydantoin or elemental iodine was found in the regenerated product.

Example 4

Example 4 obtained 23.9 g of a regenerated product with use of a reaction container identical to the reaction container used in Example 3 except that 136.0 g of ion-exchange water and 34.0 g of methanol were fed into the reaction container as a mixed solvent. A regenerated product obtained was pale yellow, and had a color tone having an $L^*$ value of 87.22, an $a^*$ value of 1.15, and a $b^*$ value of 16.24. The regenerated product contained 1,3-diiodo-5,5-dimethylhydantoin in a content of 98.5 weight %, and the yield was 86.2%. No 5,5-dimethylhydantoin or elemental iodine was found in the regenerated product.

Example 5

Example 5 produced a halohydantoin compound by treating, with a mixed solvent of an organic solvent and water, the dried product obtained in Production Example 2 above and including a halohydantoin compound.

First, air inside of a reaction container equipped with a stirrer, a thermometer, a dropping funnel, and a solid input inlet and having a capacity of 300 ml was substituted sufficiently with nitrogen. Next, ion-exchange water (27.2 g) was put into the reaction container through the dropping funnel, and then butyl acetate (142.8 g) was put into the reaction container through the dropping funnel so that the ion-exchange water and the butyl acetate were fed into the reaction container as a mixed solvent. The inside of the reaction container was then cooled to 2° C. After that, 30.0 g of the dried product (including 1,3-diiodo-5,5-dimethylhydantoin in a content of 94.2 weight %) that was obtained by the method of Production Example 2 above and that was brown (with a color tone having an $L^*$ value of 65.44, an $a^*$ value of 6.69, and a $b^*$ value of 13.02) was put into the reaction container. A content of the reaction container at this stage had a pH of 2.3.

The content of the reaction container was supplied under reduced pressure over a duration of 10 seconds onto a Nutsche that included a suction bottle and a qualitative filter paper (No. 2, available from ADVANTEC) attached to the suction bottle and that had an inner diameter of 55 mm. Then, suction was continued for 5 minutes. The sucked product showed good filterability. Crystal on the filter paper was washed with water (30 g), and then the suction was continued for 20 minutes. Next, the reduced pressure was returned to an ordinary pressure, and 30.3 g of a wet material on the filter paper was taken out. The wet material thus obtained was dried with use of an evaporator under reduced pressure (at 4 kPa and 80° C. for 30 minutes). As a result, 25.5 g of a regenerated product was obtained. The regenerated product obtained was pale yellow, and had a color tone having an $L^*$ value of 87.19, an $a^*$ value of 1.14, and a $b^*$ value of 16.64. The regenerated product contained 1,3-diiodo-5,5-dimethylhydantoin in a content of 98.0 weight %, and the yield was 88.4%. No 5,5-dimethylhydantoin or elemental iodine was found in the regenerated product.

Comparative Example 1

Comparative Example 1 was conducted with use of a reaction container similar to the reaction container used in Example 1. Butyl acetate (150.1 g) was fed into the reaction container through a dropping funnel. The inside of the reaction container was then cooled to 2° C. After that, 30.2 g of a dried product (including 1,3-diiodo-5,5-dimethylhydantoin in a content of 91.0 weight %) that was obtained by a method identical to the method of Production Example 1 and that was brown (with a color tone having an L* value of 55.14, an a* value of 5.47, and a b* value of 8.73) was put into the reaction container. While a temperature of the inside of the reaction container was maintained at 2 to 5° C., a content of the reaction container was stirred for 30 minutes. The content of the reaction container was supplied under reduced pressure over a duration of 5 minutes onto a Nutsche that included a suction bottle and a qualitative filter paper (No. 2, available from ADVANTEC) attached to the suction bottle and that had an inner diameter of 55 mm. Then, suction was continued for 5 minutes. The sucked product showed good filterability. Crystal on the filter paper was washed with 31.2 g of water, and then the suction was continued for 30 minutes. Next, the reduced pressure was returned to an ordinary pressure, and 25.7 g of a wet material on the filter paper was taken out. The wet material thus obtained was dried with use of an evaporator under reduced pressure (at 4 kPa and 80° C. for 30 minutes). As a result, 22.8 g of a regenerated product was obtained. The regenerated product obtained contained 1,3-diiodo-5,5-dimethylhydantoin in a content of 98.0 weight %. However, the regenerated product was brown, and had a color tone having an L* value of 57.82, an a* value of 9.03, and a b* value of 13.30. The regenerated product was not decolorized at all.

As described above, Comparative Example 1 washed, with use of only an organic solvent, a composition including a halohydantoin compound. As a result, the regenerated product obtained, although having increased purity, had unpreferable coloring.

Comparative Example 2

Comparative Example 2 was conducted with use of a reaction container similar to the reaction container used in Example 1. Ion-exchange water (150.0 g) was fed into the reaction container through a dropping funnel. The inside of the reaction container was then cooled to 2° C. After that, 30.2 g of a dried product (including 1,3-diiodo-5,5-dimethylhydantoin in a content of 91.0 weight %) that was obtained by a method identical to the method of Production Example 1 and that was brown (with a color tone having an L* value of 55.14, an a* value of 5.47, and a b* value of 8.73) was put into the reaction container. While a temperature of the inside of the reaction container was maintained at 2 to 5° C., A content of the reaction container was stirred for 30 minutes. The content of the reaction container was supplied under reduced pressure over a duration of 5 minutes onto a Nutsche that included a suction bottle and a qualitative filter paper (No. 2, available from ADVANTEC) attached to the suction bottle and that had an inner diameter of 55 mm. Then, suction was continued for 5 minutes. The sucked product showed good filterability. Crystal on the filter paper was washed with 31.2 g of water, and then the suction was continued for 30 minutes. Next, the reduced pressure was returned to an ordinary pressure, and 25.7 g of a wet material on the filter paper was taken out. The wet material thus obtained was dried with use of an evaporator under reduced pressure (at 4 kPa and 80° C. for 30 minutes). As a result, 22.8 g of a regenerated product was obtained. The regenerated product obtained contained 1,3-diiodo-5,5-dimethylhydantoin in a content of 98.0 weight %. However, the regenerated product was brown, and had a color tone having an L* value of 55.14, an a* value of 5.47, and a b* value of 8.73. The regenerated product was not decolorized at all.

As described above, Comparative Example 2 used only ion-exchange water as a liquid for cleaning a composition including a halohydantoin compound. As a result, the regenerated product obtained, although having increased purity, had unpreferable coloring.

INDUSTRIAL APPLICABILITY

The present invention is suitably applicable to a method for producing a halohydantoin compound for use as (i) a sensitizer for a photograph and the like, (ii) a halogenating agent or oxidizing agent for a process of producing a medicinal product, an agricultural chemical, a compound and the like, or (iii) an iodizing reagent.

The invention claimed is:
1. A method for purifying a halohydantoin compound in which method a composition including a halohydantoin compound and an impurity is treated,
the method comprising the step of:
washing the composition by adding the composition to a solvent mixture of water and an organic solvent and washing the composition with the solvent mixture; and
isolating a halohydantoin composition with reduced impurity content;
wherein the composition includes an impurity in an amount within a range of not less than 4 weight % and not greater than 30 weight % relative to the weight of the composition,
wherein:
the halohydantoin compound is represented by the following chemical formula I:

Chem. 1,

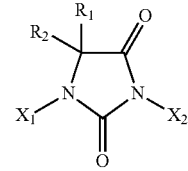

(I)

where
$R_1$ and $R_2$ are either identical to or different from each other, and are each independently H, or a C1 to C8 aliphatic hydrocarbon group; and
$X_1$ and $X_2$ are both I.
2. The method according to claim 1,
wherein:
the impurity is at least one of elemental halogen, a hydantoin compound, and an inorganic salt.
3. The method according to claim 1,
wherein the composition has an L* value of not greater than 70, an a* value of not less than 5, and a b* value of not greater than 14 in the L*a*b* color system (CIE 1976 L*a*b* color space).
4. The method according to claim 1,
wherein:
the organic solvent is at least one of an ester solvent, an alcohol solvent, an aromatic solvent, an ether solvent, and a chlorinated solvent, each having a boiling point of not less than 30° C. and not greater than 200° C.

5. The method according to claim 1,
wherein:
during the step of washing, the mixed solvent has a temperature of not less 10° C. and not greater than 50° C.

6. The method according to claim 1,
wherein:
the halohydantoin compound is represented by the following chemical formula I:

Chem. 1,

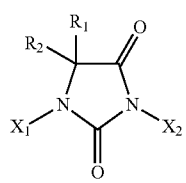 (I)

where
$R_1$ and $R_2$ are either identical to or different from each other, and are each independently H or a methyl group; and $X_1$ and $X_2$ are both I.

7. A method for producing a halohydantoin compound in which method a composition including a halohydantoin compound and an impurity is treated, the method comprising the step of:

obtaining the composition including the halohydantoin compound by reacting a hydantoin compound and iodine monochloride with each other in an aqueous solution in the presence of a base; and purifying the halohydantoin compound by the method according to claim 1.

* * * * *